United States Patent [19]

Matravers

[11] Patent Number: 4,725,433
[45] Date of Patent: Feb. 16, 1988

[54] NOVEL HAIR CONDITIONER

[75] Inventor: Peter Matravers, Los Angeles, Calif.

[73] Assignee: Neutrogena Corporation, Los Angeles, Calif.

[21] Appl. No.: 891,747

[22] Filed: Jul. 31, 1986

[51] Int. Cl.⁴ .............................................. A61K 7/06
[52] U.S. Cl. ........................................ 424/70; 424/78; 514/938
[58] Field of Search ............................................ 424/70

[56] References Cited

U.S. PATENT DOCUMENTS 2,742,396  4/1956  Sperandio et al. .................. 514/969

FOREIGN PATENT DOCUMENTS 1111350  10/1981  Canada .................................. 424/70
0149249  7/1985  European Pat. Off. ............... 424/70
243010  12/1985  Japan ..................................... 424/70

*Primary Examiner*—Dale R. Ore
*Attorney, Agent, or Firm*—Richard R. Mybeck

[57] ABSTRACT

A substantially homogeneous oil-free, fatty alcohol-free hair conditioner base comprising, in weight percent, from about 0.5 to about 3.0 percent Laureth-4; from about 1 to about 4 percent of Choleth 24; from about 0.1 to about 0.8 percent hydroxyethylcellulose; from about 0.4 to about 0.8 percent Polyquaternium 10; and a solvent selected from the group consisting of purified water and a water-alcohol mixture. Cationic/anionic grooming agents, moisturizing agents, viscosity modifiers, preservatives, and fragrance can be added to form hair care products therefrom.

31 Claims, No Drawings

NOVEL HAIR CONDITIONER

INTRODUCTION

The present invention relates to substantially homogeneous oil-free, fatty alcohol-free hair conditioner base containing as key ingredients a polyethylene glycol (24) cholesteryl ether, a derivative of ethoxylated cholesterol (CTFA name: Choleth-24); and a polyethylene glycol ether of lauryl alcohol (CTFA name: Laureth-4).

BACKGROUND OF INVENTION

Most conventional hair conditioners are either poorly formulated or too substantive and produce undesirable "buildup" and over conditioning after extended use. In addition, these conditioners required a very delicate and sensitive emulsification/micell formation to form a cationic conditioner base and as a result, the production thereof is both time consuming and costly.

The prior art conditioner bases, that is, those carrier compositions which accept and dispense hair conditioning reagents, usually contained stearalkonium chloride or its equivalent and as such effectively precluded the use of many anionic polymers known to provide certain desirable properties such as strengthening the hair fibers and improving the hold of the hair.

A need currently exists for a new conditioner base which overcomes the arduous procedures of the prior methods, eliminates the undesirable build-up on the user's hair which characterized the prior formulations, and which provides a stable product which substantially enhances combing and the feel of the human hair while substantially eliminating those deleterious and unattractive results obtained by prior formulations when used over extended periods of time.

The present invention is predicated upon fulfilling those needs with a homogeneous water-based clear, safe and effective hair conditioner base which eliminates the oils and waxes heretofore contained in those opaque prior art conditioners which required the presence of fatty alcohols, such as cetyl and cetearyl, and stearalkonium chloride. The present invention further provides a conditioner having surprisingly desirable results when confronted with curl retention and blow drying challenges. This disclosure represents a further improvement over my previous U.S. patent application Ser. No. 722,964 filed Apr. 12, 1985 now U.S. Pat. No. 4,610,874.

SUMMARY OF INVENTION

The present invention is directed to a novel homogeneous water-based, clear, freely pourable, cationic hair conditioner base which is free of both oil and fatty alcohols and when formulated, as hereinafter described, into a finished conditioner, provides a product which materially reduces residual deposits on the hair even after extensive use, enhances curl retention, and resists deterioration of hair by contemporary blow driers. More particularly the present invention provides a new and improved hair conditioner formulation having enhanced conditioning and aesthetic qualities which contains as essential ingredients a derivative of an ethoxylated cholesterol and a polyethylene glycol ether of lauryl alcohol. In addition to improving both the feel and the combability of the human hair with which it is used, the new conditioner base shows high rinseability and substantially no build up even when used over extended periods of time.

The salient feature of this invention is the unique combination of the derivatives of ethoxylated cholesterol and a polyethylene glycol ether of lauryl alcohol with special cationic polymers which allows other lanolin derivatives, hydrolyzed animal protein, and the like to be readily blended thereinto to enhance the performance thereof without adversely affecting either the clarity or the mildness thereof. These and other additives may be readily employed to add body, shine and manageability to the hair without creating the reagent buildup and its accompanying dinginess which characterized prior art formulations.

Accordingly, a principal object of the present invention is to provide a new and improved hair conditioner which is both oil and fatty alcohol free and sustains curl in permanent wave treated hair.

Another object of the present invention is to provide a new and improved hair conditioner which avoids the undesirable buildup characterizing repeated use of currently available substantive conditioners.

A further object of the present invention is to provide an oil free, fatty alcohol free hair conditioner which provides both body and lubricity for easy combing, which allows the incorporation of a variety of anionic or cationic ingredients thereinto without detracting therefrom, and which helps protect hair from frequent use of contemporary blow driers.

Still another object of the present invention is to provide an improved conditioner base which is water soluble and readily delivers conditioner reagents to the hair to provide the benefits thereof without incurring either eye irritation or the deleterious side and after effects which characterize those conditioners using oils, fatty alcohols, and stearalkonium chloride as delivery media.

These and still further objects as shall hereinafter appear are readily fulfilled by the present invention in a remarkably unexpected manner as will be readily discerned from the following detailed description of an exemplary embodiment thereof.

DESCRIPTION OF PREFERRED EMBODIMENTS

In one practice of the present invention, a composition is formulated by introducing into a batch blender while providing continuous agitation an amount of a polymeric quaternary ammonium salt of hydroxyethylcellulose reacted with a trimethyl/ammonium substituted epoxide (CTFA name: Polyquaternium 10), hydroxyethylcellulose, and purified water and heating the mixture to about 75° C. Thereafter, an amount of polyethylene glycol (24) cholesteryl ether i.e., the polyethylene glycol ether of cholesterol having an average ethoxylation value of 24 (CTFA name: Choleth 24) and a polyethylene glycol ether of lauryl alcohol (CTFA name: Laureth-4) is added while maintaining both the stirring and the temperature. When a homogeneous mixture of the conditioner base is obtained, any of a variety of known conditioning agents can be blended into the mixture as desired to achieve such other end properties as may be desired for the ultimate commercial formulation. Included among such additives found compatible with this base formulation are polyvinyl pyrrolidone ("PVP") for body and hold; Laneth 16 (the polyethylene glycol ether of lanolin alcohol (q.v.) with an average ethyoxylation value of 16) for sheen; propylene glycol for shine, and the like. Cationic conditioning agents which are compatible with the conditioner base hereof include Polyquaternium-5, Quaternium 7 (steapyrium chloride), Polyquaternium-7, Polyquaternium-11, Quaternium-26, Olealkonium Chloride, Cetrimonium Chloride, quaternized hydrolyzed animal proteins and the like.

CTFA adopted names, when available, are used throughout this disclosure. CAS Numbers, RD Numbers, definitions and other names are printed in the "CTFA Cosmetic Ingredient Dictionary" 3rd edition, Published by The Cosmetic, Toiletry and Fragrance Association, 1110 Vermont Avenue, N.W., Washington, D.C. 20005.

Non-ionic moisturizing ingredients useful herein include sodium pyroglutamate (aka sodium PCA) glycerin, soluble collagen, hydrolyzed animal protein, panthenol, and the like. After the desired conditioning ingredients and appropriate preservatives are blended into the batch, the batch is cooled to ambient temperature, the fragrance added, and the formulation is ready for packaging.

A representative formulation embodying the present invention will contain in percent by weight from about 0.1 to about 0.8 percent hydroxyethylcellulose (Natrosol ®, Hercules); from about 0.5 percent to about 3.0 percent Laureth-4; from about 1 to about 4 percent polyethylene glycol (24) cholestrol ether (Choleth 24); from about 0.1 to about 2 percent of polyethylene glycol (16) lanolin ether (Laneth 16); from about 0.4 to about 0.8 percent polyquaternium 10; from about 1 to about 4 percent Quaternium 76 Hydrolyzed Animal Protein (Lexein QX 3000, Inolex); from about 0.2 to about 0.8 percent PVP; from about 0.1 to about 0.15 percent methylparaben, about 0.05 percent propylparaben, about 0.1 to about 0.3 percent imidazolidinyl urea; about 2 to about 8 percent propylene glycol; about 0.2 to about 0.5 percent fragrance; and qs purified water.

Further, viscosity modifiers such as synthetic gum, guar gum and the like have been found both compatible and useful in the formulation hereof.

Other recognized reagents for hair care products which can be employed successfully in the conditioner base of the present invention and the function they fulfill are: vinylpyrrolidone/vinyl acetate copolymers (PVP/VA) which are film formers, hair thickeners, and hair styling promoters; agents AT845, AT937 and AT958 (also known as copolymers 845, 937 and 958, respectively) which impart a pleasant "feel" and enhance hold and curl retention; silicone glycol copolymers (available as Dow fluids 190 and 193), ethylene oxide polymers (available as Polyox), and Guar hydroxypropyltrimonium chloride (available as Jaguar C-17), which are detangling agents; keratin amino acids (also known as "Croteins") which improve hair strength and manageability; Quaternium 22 (available as "Ceraphyl 60") steapyrium chloride (EMCOL E607S) and polyquaternium 40 (available as "Merquat 100") which enhance manageability and prevent flyaway; and sodium isostearoyl-2-lactylate (available as "Pationic ISL") which provide improved feel and moisture.

As will appear, the conditioner base of this invention, because of its base, enjoys the versatility of allowing many cationic and anionic ingredients to be added thereto without upsetting either the stability or the balance of the base. Furthermore, as will hereinafter appear, the specific formulation of the present invention provides improved curl retention and blow driability.

To further aid in the understanding of the present invention, and not by way of limitation, the following examples are presented.

EXAMPLE I

With continuous mixing, hydroxyethylcellulose and Polyquaternium 10 are dispensed into purified water and heated to 75° C. While maintaining the temperature at 75° C., the desired amount of Choleth 24, Laureth-4, and Laneth 16 are blended into the water-cellulose mixture to form a homogeneous blend. The type and level of specific conditioning agents are then selected and blended into the blend, e.g., Polyquaternium 10, glycerin, PVP and the like. The batch is thereafter cooled to ambient temperature. Thereafter the desired amounts of fragrance and anhydrous ethyl alcohol (e.g., SD 40), if any, are added and the formulation, shown below by weight percent, is ready for packaging. The formulation provided a clear, freely pourable solution which is free of both oil and fatty alcohol.

| Purified Water | 83.82% |
| --- | --- |
| Hydroxyethylcellulose | .85% |
| Polyquaternium 10 | .8% |
| Choleth 24 | 2.0% |
| Laureth-4 | 0.5% |
| PVP (K30) | .5% |
| Citric acid 50% | .03% |
| Methylparaben | .15% |
| Propylparaben | .05% |
| Imidazolidinyl Urea | .3% |
| Propylene glycol | 5.0% |
| Polyquaternium-11 | 2.0% |
| Sodium PCA | 3.0% |
| Glycerin | 1.0% |

EXAMPLE II

Following the procedure of Example I, a clear, freely pourable, oil-free, fatty alcohol-free hair conditioner was prepared having the following formulation in percent by weight.

| Purified Water | 73.37% |
| --- | --- |
| Hydroxyethylcellulose | .7% |
| Polyquaternium-10 | .6% |
| Choleth 24 | 2.0% |
| Laureth-4 | 2.0% |
| PVP (K30) | .3% |
| Citric acid 50% | .03% |
| Methylparaben | .15% |
| Propylparaben | .05% |
| Imidazolidinyl Urea | .3% |
| Propylene glycol | 8.0% |
| Fragrance | .5% |
| SD 40 Alcohol | 12.0% |

EXAMPLE III

Following the procedure of Example I, a clear, freely pourable, oil-free, fatty alcohol-free hair conditioner was prepared having the following formulation in percent by weight.

| Purified Water | 78.27% |
| --- | --- |
| Hydroxyethylcellulose | .8% |
| Polyquaternium-10 | .6% |
| Laureth-4 | 1.0% |
| Choleth 24 | 2.0% |
| PVP (K30) | .3% |
| Citric acid 50% | .03% |

-continued

| | |
|---|---|
| Methylparaben | .15% |
| Propylparaben | .05% |
| Imidazolidinyl Urea | .3% |
| Propylene glycol | 4.0% |
| Fragrance | .5% |
| SD 40 Alcohol | 12.0% |

EXAMPLE IV

A conditioner was prepared according to the procedure of Example I, having a composition, in weight percent, of:

| | |
|---|---|
| Purified Water | 73.72% |
| Hydroxyethylcellulose | .75% |
| Polyquaternium-10 | .5% |
| Choleth 24 | 2.0% |
| Laureth-4 | 1.0% |
| PVP (K30) | .4% |
| Laneth-16 | .4% |
| Citric acid 50% | .03% |
| Methylparaben | .15% |
| Propylparaben | .05% |
| Imidazolidinyl Urea | .3% |
| Propylene glycol | 6.0% |
| SD 40 Alcohol | 12.0% |
| Fragrance | .20% |
| Steapyrium chloride | .50% |
| Quaternium-76 Hydrolyzed Animal Protein | 2.0% | was compared with a commercial product (AGREE ®, regular conditioner) in a modified Draize Eye Irritation study. The Modified Draize Eye Test (See: 16 CFR 1500.42 and "Recommended Guidelines for Acute Eye Irritation Testing", Interagency Regulatory Liason Group 1981). The tests, performed in accordance with the cited references, involved nine (9) New Zealand albino rabbits whose eyes were adjudged free from occular defects. The test material was instilled into the conjunctival sac of each of six (6) animals, the lids held together for one (1) second, after which the rabbits were returned to their cages. The remaining three animals were tested in the same manner except that the test material was flushed from the eye with 140 ml of water after an exposure period of five (5) seconds. The untreated eye in each rabbit served as a control. Occular irritation was evaluated at twenty-four (24), forty-eight (48), seventy-two (72) hours and, if any occular irritation was present at 72 hours, at seven (7) days in accordance with the grading scale shown below.

| | IRRITATION RATING | |
|---|---|---|
| RATING | RANGE OF MEAN SCORE | DEFINITION |
| Non-Irritating | 0.0–0.5 | To maintain this rating, all scores at the 48-hour reading must be zero; otherwise increase rating one level. |
| Practically Non-Irritating | Greater than 0.5–2.5 | To maintain this rating, all scores at the 48-hour reading must be zero; otherwise increase rating one level. |
| Minimally Irritating | Greater than 2.5–15.0 | To maintain this rating, all scores at the 72-hour reading must be zero; otherwise increase rating one level. |
| Mildly Irritating | Greater than 15.0–25.0 | To maintain this rating, all scores at the 7-day reading must be zero; otherwise increase rating one level. |
| Moderately irritating | Greater than 25.0–50.0 | To maintain this rating, scores at 7 days must be less than or equal to 10 for 60% or more of the animals. Also mean 7-day score must be less than or equal to 20 and more than 60% of animals show scores less than 10, then no animal among those showing scores greater than 10 can exceed a score of 30 if rating is to be maintained; otherwise, increase rating one level. |
| Severely Irritating | Greater than 50.0–80.0 | To maintain this rating, scores at 7 days must be less than or equal to 30 for 60% or more of the animals. Also mean 7-day score must be less than or equal to 40. If 7-day mean score is less than or equal to 40 and more than 60% of the animals show scores less than 10 or equal to 30, then no animal among those showing scores greater than 30 can exceed a score of 60 if rating is to be maintained; otherwise, increase rating one level. |
| Extremely Irritating | Greater than 80.0–110.0 | |

The samples were tested undiluted with 0.1 ml instilled into each eye tested. The results obtained are reported in Table A. The label contents of AGREE ® conditioner are: water; cetyl alcohol; stearalkonium chloride; dimethylstearamine; cetrimonium chloride; propylene glycol; hydroxyethyl cellulose; fragrance; preservatives; and FD & C colors.

TABLE A

| | TEST SAMPLE | | AGREE ® CONDITIONER | |
|---|---|---|---|---|
| Time Hour/day | Unwashed Eyes | Washed Eyes | Unwashed Eyes | Washed Eyes |
| 24 hrs | 1.0 | 0 | 8.66 | 3.64 |
| 48 hrs | 0 | 0 | 4.33 | 1.34 |
| 72 hrs | 0 | 0 | 2.64 | 0 |
| 7 days | 0 | 0 | 1.00 | 0 |
| Rating: | Practically Non-irritating | Non-irritating | Moderately Irritating | Minimally Irritating |

EXAMPLE V

Additional testing was conducted to compare the conditioner prepared according to Example IV with a commercially available product (AGREE ® conditioner). The label contents of AGREE ® conditioner are: water; cetyl alcohol; stearalkonium chloride; dimethylstearamine; cetrimonium chloride; propylene glycol; hydroxyethyl cellulose; fragrance; preservatives; and FD & C colors. Protocol denominated "Modified CFR Ocular Instillation Test", "CFR Primary Skin Irritation Test" and "Acute Oral Toxicity Test" were employed. Both products passed the primary skin irritation and acute oral toxicity test with little difference in results. In the Modified CFR Ocular Irritation Test, nine healthy New Zealand white rabbits were used. Both eyes were examined at 0 hour and each was assigned a score. 0.2 milliliters of the substance to be tested was instilled into the right eye of each of the nine rabbits. The left eye was untreated and served as the control. For three of the rabbits in each set, the eye was rinsed with normal saline immediately following the administration of the tested substance. Thereafter, both eyes were examined at 24, 48 and 72 hours post-instillation. As shown in TABLE B below, the conditioner embodying the present invention was notably safer and milder (slight redness in only one or nine test animals) than was the commercial product (caused redness and chemosis in five of nine test animals).

TABLE B

| Rabbit | | Observations (hours post-instillation) | | | |
|---|---|---|---|---|---|
| | | 0 | 24 | 48 | 72 |
| Tested substance: Example IV | | | | | |
| 101 | Test | 0 | A | 0 | A |
| | Control | 0 | 0 | 0 | 0 |
| 102 | Test | 0 | 0 | 0 | 0 |
| | Control | 0 | 0 | 0 | 0 |
| 103 | Test | 0 | 0 | 0 | 0 |
| | Control | 0 | 0 | 0 | 0 |
| 104 | Test | 0 | 0 | 0 | 0 |
| | Control | 0 | 0 | 0 | 0 |
| 105 | Test | 0 | 0 | 0 | 0 |
| | Control | 0 | 0 | 0 | 0 |
| 106 | Test | 0 | 0 | 0 | 0 |
| | Control | 0 | 0 | 0 | 0 |
| 107R | Test | 0 | 0 | 0 | 0 |
| | Control | 0 | 0 | 0 | 0 |
| 108R | Test | 0 | 0 | 0 | 0 |
| | Control | 0 | 0 | 0 | 0 |
| 109R | Test | 0 | 0 | 0 | 0 |
| | Control | 0 | 0 | 0 | 0 |
| Tested substance: AGREE ® | | | | | |
| 201 | Test | 0 | A,B | A | 0 |
| | Control | 0 | 0 | 0 | 0 |
| 202 | Test | 0 | A | A | A |
| | Control | 0 | 0 | 0 | 0 |
| 203 | Test | 0 | A° | A | A |
| | Control | 0 | 0 | 0 | 0 |
| 204 | Test | 0 | 0 | 0 | 0 |
| | Control | 0 | 0 | 0 | 0 |
| 205 | Test | 0 | A | A | 0 |
| | Control | 0 | 0 | 0 | 0 |
| 206 | Test | 0 | A° | A | 0 |
| | Control | 0 | 0 | 0 | 0 |
| 207R | Test | 0 | 0 | 0 | 0 |
| | Control | 0 | 0 | 0 | 0 |
| 208R | Test | 0 | 0 | 0 | 0 |
| | Control | 0 | 0 | 0 | 0 |
| 209R | Test | 0 | 0 | 0 | 0 |
| | Control | 0 | 0 | 0 | 0 |

Code:
0 = No reaction
A = (IIIA1) = Conjunctivae, Redness, Some vessels definitely injected
R = Rinsed
B = (IIIB1) Chemosis, above normal swelling (includes nictitating membranes)
° = slight mucous discharge

EXAMPLE VI

A conditioner was prepared according to the procedure of Example I having a composition, in weight percent of:

| | |
|---|---|
| Purified Water | 72.8% |
| Hydroxyethylcellulose | .6% |
| Polyquaternium 10 | .5% |
| Choleth 24 | 2.0% |
| PVP (K30) | .4% |
| Solulan 16 | .4% |
| Laureth-4 | 1.5% |
| Methylparaben | .15% |
| Propylparaben | .05% |
| Imidazolidnyl urea | .3% |

-continued

| | |
|---|---|
| Propylene glycol | 6.0% |
| Fragrance | .3% |
| SD 40 Alcohol | 15.0% |

Like amounts of commercially available conditioners were obtained and all test samples were spiked with fluorescein, a special fluorescent dye. Swatches were prepared with virgin hair and damaged hair (i.e., perm treated). The conditioner was applied to the several hair swatches and after the prescribed time, rinsed therefrom. Measurements were then taken to determine the residue (in percent) remaining on the hair after the prewash (rinse). The results using ten swatches and taking the average of three trials are reported in Table C. The label contents of the several commercially available conditioners are: FLEX ® (Revlon) contains: water, Stearalkonium Chloride, Cetyl Alcohol, Polysorbate 60, PEG-150 Stearate, Steareth-20, Hydrolyzed Animal Protein, Cetearyl Alcohol, Balsam Canada, Preservatives and Colors. SILKIENCE ® (Gillette) contains: water, Ceteth-2, Stearalkonium Chloride, Citric Acid, Fragrance, Dimethyl Stearamine Citrate, Glyceryl Stearate, Phenoxyethanol, Sodium Chloride, Stearyl Alcohol, Monosodium Citrate, FD&C colors. SILKIENCE ® EXTRA (Gillette) contains: water, Ceteth-2, Stearalkonium Chloride, Citric Acid, Dimethyl Stearamine Citrate, Glyceryl Stearate, Steartrimonium Hydrolyzed Animal Protein, Phenoxyethanol, Stearyl Alcohol, Fragrance, Preservatives and colors. CLAIROL ® (Clairol, Inc.) contains: water, Glycerol Stearate, Acetamide MEA, Stearalkonium Chloride, Cetyl Alcohol, Polysorbate 20, Hydrolyzed Animal Protein, Fragrance, Hydrolyzed Keratin, Hydroxyethyl Cellulose, Preservatives, FD&C colors. CLAIROL ® EXTRA (Clairol, Inc.) contains: water, Glycol Stearate, Acetamide MEA, Hydrolyzed Animal Protein, Stearalkonium Chloride, Cetyl Alcohol, Hydroxyethyl Cellulose, Fragrance, Preservatives and colors. AGREE ® (Johnson and Son) contains: water, Cetyl Alcohol, Stearalkonium Chloride, Dimethylstearamine, Cetrimonium Chloride, Propylene Glycol, Hydroxyethyl Cellulose, Fragrance, Preservatives, FD&C colors. AGREE ® EXTRA contains: water, 1-Hexadecanol, Stearalkonium Chloride, Hydroxyethyl Cellulose, Fragrance, Preservatives and colors, L'OREAL ® Protein (Cosmoir, Inc.) contains: water, Hydroxyethyl cellulose, Ceteth-1, Stearalkonium Chloride, Dicetyldimonium Chloride, Fragrance, Preservatives and colors. L'OREAL ® Regular (Cosmoir, Inc.) contains: water, Hydroxyethyl cellulose, Ceteth-1, Stearalkonium Chloride, Quaternium-31, Fragrance, Preservatives and colors. IVORY ® (Procter & Gamble) contains: water, Stearalkonium Chloride, Cetyl Alcohol, Stearyl Alcohol, Ceteth-2, Glyceryl Stearate, Steartrimonium, Hydrolyzed Animal Protein, Preservatives and colors, Fragrance. FINESSE ® (Helene Curtiss) contains: water, Cetyl Alcohol, Dicetyldimonium Chloride, Cyclomethicone, Stearyl Alcohol, Ceteareth-20, Propylene Glycol, Stearamidopropyl Dimethylamine, Fragrance, Preservatives and colors.

TABLE C

| Specimen | Residue (Average % remaining) | |
|---|---|---|
| | Virgin Hair | Damaged Hair |
| FLEX ® (Revlon) | 0.668± | 1.209 |
| SILKIENCE ® (Gillette) | 1.511± | 1.652 |
| SILKIENCE ® (Gillette) | 2.375± | 2.384 |
| CLAIROL ® (Clairol, Inc.) | 0.635± | 0.907 |
| CLAIROL ® EXTRA (Clairol, Inc) | 1.090± | 1.294 |
| AGREE ® (Johnson and Son) | 0.547± | 0.972 |
| AGREE ® EXTRA (Johnson and Son) | 0.634± | 1.268 |
| L'OREAL ® Protein (Cosmoir, Inc.) | 0.796± | 1.103 |
| L'OREAL ® Regular (Cosmoir, Inc.) | 0.640± | 0.842 |
| IVORY ® (Procter & Gamble) | 1.223± | 1.601 |
| FINESSE ® (Helene Curtiss) | 0.896± | 1.347 |
| EXAMPLE VI | 0.462± | 0.562 |

From the foregoing, it is apparent that the material prepared according to the present invention produced a highly acceptable level of conditioning residue after rinse (Prewash residue).

EXAMPLE VII

The test samples used in Example VI were further tested to determine the ability for the several conditioners to be removed by shampooing (Wash 1, Wash 2, etc.) as a measure of "conditioner build-up". The results are reported in Table D-1 and D-2.

TABLE D-1

| | Virgin Hair | | | |
|---|---|---|---|---|
| | Residue (Average % remaining) | | | |
| Specimen | Wash 1 | Wash 2 | Wash 3 | Wash 4 |
| FLEX ® | .237 | .071 | | |
| SILKIENCE ® EXTRA | .620 | .345 | .121 | .030 |
| SILKIENCE ® | .358 | .141 | .047 | |
| CLAIROL ® | .225 | .106 | | |
| CLAIROL ® EXTRA | .699 | .435 | .111 | |
| AGREE ® | .174 | .079 | | |
| AGREE ® EXTRA | .241 | .132 | .041 | |
| L'OREAL ® Protein | .424 | .189 | .077 | |
| L'OREAL ® Regular | .234 | .097 | | |
| IVORY ® | .844 | .485 | .301 | .141 |
| FINESSE ® | .407 | .223 | .068 | |
| EXAMPLE VI | .028 | | | |

TABLE D-2

| | Damaged Hair | | | |
|---|---|---|---|---|
| | Residue (Average % remaining) | | | |
| Specimen | Wash 1 | Wash 2 | Wash 3 | Wash 4 |
| FLEX ® | .812 | .406 | .244 | .087 |
| SILKIENCE ® EXTRA | 1.811 | 1.355 | .824 | .389 |
| SILKIENCE ® | 1.031 | .675 | .315 | .094 |
| CLAIROL ® | .516 | .210 | .067 | |
| CLAIROL ® EXTRA | 1.294 | .722 | .419 | .211 |
| AGREE ® | .618 | .324 | .122 | |
| AGREE ® EXTRA | .785 | .361 | .161 | |
| L'OREAL ® Protein | .665 | .307 | .140 | |
| L'OREAL ® Regular | .504 | .262 | .034 | |
| IVORY ® | .894 | .363 | .245 | .080 |
| FINESSE ® | .772 | .310 | .167 | |
| EXAMPLE VI | .183 | .072 | | |

In each test the conditioner produced according to the present invention (Example VI) was readily and completely removed with only one or two washings thereby preventing conditioner buildup.

EXAMPLE VIII

A sample prepared pursuant to Example VI was traced through a sequence of seven conditioning and shampoo cycles and the residues measured using the florescein previously described. Similar data was accumulated for the commercially available conditioners sold under the brand names AGREE ®, FINESSE ®, CLAIROL ®, CLAIROL ® EXTRA, and SILKIENCE ® EXTRA having the ingredients reported above. The results, which unequivocally demonstrate a significantly reduced buildup of residues after extended use by the present invention, are reported in Table E.

TABLE E

| | Residue remaining after each conditioning/shampoo cycle | | | |
|---|---|---|---|---|
| Specimen | Cycle 1 | Cycle 2 | Cycle 3 | Cycle 4 |
| SILKIENCE ® EXTRA | 2.342 | 2.971 | 3.582 | 3.976 |
| CLAIROL ® | .644 | .806 | .911 | 1.052 |
| CLAIROL ® EXTRA | 1.203 | 1.788 | 1.917 | 2.018 |
| AGREE ® | .212 | .309 | .468 | .622 |
| FINESSE ® | .855 | 1.134 | 1.267 | 1.434 |
| EXAMPLE VI | .096 | .146 | .217 | .203 |

| | Cycle 5 | Cycle 6 | Cycle 7 |
|---|---|---|---|
| SILKIENCE ® EXTRA | 4.068 | 4.040 | 4.102 |
| CLAIROL ® | 1.033 | 1.045 | 1.037 |
| CLAIROL ® EXTRA | 2.137 | 2.244 | 2.303 |
| AGREE ® | .814 | .944 | .930 |
| FINESSE ® | 1.469 | 1.411 | 1.404 |
| EXAMPLE VI | .222 | .216 | .236 |

EXAMPLE IX

Three commercially available conditioners were selected for comparative testing with the conditioner of Example IV and a distilled water control.

The first (SILKIENCE ®, Gillette, Co.) contained water, Ceteth-2 (the propylene glycol ether of cetyl alcohol having the formula $(CH_3)(CH_2)_{14}CH_2(OCH_2CH_2)_nOH$ where "n" has an average value of 2), stearalkonium chloride, citric acid, fragrance, stearamine citrate, glyceryl stearate, phenoxyethanol, sodium chloride, stearyl alcohol, monosodium citrate, and FD&C colors.

The second (CLAIROL ®, Clairol, Inc.) contained water, glycol stearate, acetamide MEA, stearalkonium chloride, cetyl alcohol, polysorbate 20, hydrolyzed animal protein, fragrance, hydrolyzed keratin, hydroxyethyl cellulose, preservatives, and FD&C colors.

The third (AGREE ®, S. C. Johnson & Sons, Inc.) contained water, cetyl alcohol, stearalkonium chloride, dimethylstearamine, cetrimonium chloride, propylene glycol, hydroxyethyl cellulose, fragrance, preservatives and FD&C colors.

A first test was conducted to determine the effect of the various test samples on the curl retention of permanent wave treated hair. Hair swatches, treated first with a standard professional salon permanent, were alternately shampooed and conditioned with one of the test products. The retention of curl was determined by the overall length of the hair swatch compared to its longest length prior to permanent wave treatment and its shortest length (immediately after the initial permanent wave treatment). The results reported in Table F below indicate a correlation between curl retention and reduced residue build up.

TABLE F
Length of Hair Tresses after Conditioning (in cm)

| Treatment | Control | Clairol ® | Silkience ® | Agree ® | EX I |
|---|---|---|---|---|---|
| Perm | 17 | 17 | 17 | 17 | 17 |
| Shampoo Conditioner Cycle | 17.5 | 17.6 | 17.5 | 17.6 | 17.5 |
| 1 | 17.5 | 17.7 | 17.9 | 17.6 | 17.5 |
| 2 | 17.5 | 17.7 | 17.9 | 17.7 | 17.6 |
| 3 | 17.5 | 17.9 | 18.1 | 17.9 | 17.6 |
| 4 | 17.6 | 17.9 | 18.3 | 18.1 | 17.8 |
| 5 | 17.7 | 18.4 | 18.6 | 18.2 | 17.9 |
| 6 | 18.0 | 18.8 | 18.6 | 18.2 | 18.2 |
| 7 | 18.0 | 18.8 | 18.8 | 18.2 | 18.2 |
| 8 | 18.3 | 19.5 | 19.6 | 18.2 | 18.2 |
| 9 | 18.5 | 19.5 | 19.6 | 18.2 | 18.2 |
| 10 | 18.9 | — | — | 18.3 | 18.4 |

EXAMPLE X

Using the same specimens as used in Example IX, a study was conducted to determine whether the efficacy of commercially available conditioners is effected by thermal drying.

The conditioners were applied to virgin hair tresses and to damaged hair tresses. The virgin hair tresses were purchased from De Meo Bros., Brooklyn, N.Y. and the damaged hair was created by subjecting a portion of the virgin hair with a salon-type permanent wave solution. A total of six tresses, three virgin and three damaged, were used with each conditioner listed. All tresses were washed together in shampoo and lightly towel dried to prevent dripping. While the hair was still wet, the several conditioners were applied according to label directions. In all cases, 1.5 grams of conditioner per hair tress was used.

After treatment and drying by one of three methods: air dry; hot blow dry; and cold blow dry, the tresses were combed and randomized before submission to six trained evaluators who separately evaluated the tresses for general condition, static, shine, manageability, softness and body. Each was rated on a scale of 0-5 with 5 being the best. The results of the scoring, with the highest score being indicated by an "A" and so on through "D" for the lowest score, on each of the categories are shown in Table G1–G6, below.

TABLE G-1
AIR DRYING - NORMAL HAIR

| Specimen | Overall | Static | Shine | Manage | Soft | Body |
|---|---|---|---|---|---|---|
| AGREE ® | B | C | B | B | B | B |
| CLAIROL ® II | D | D | D | D | D | D |
| SILKIENCE ® | B | B | C | C | C | C |
| EXAMPLE IV | A | A | A | A | A | A |

TABLE G-2
AIR DRYING - DAMAGED HAIR

| Specimen | Overall | Static | Shine | Manage | Soft | Body |
|---|---|---|---|---|---|---|
| AGREE ® | C | B | B | A | B | A |
| CLAIROL ® II | B | D | C | C | A | B |
| SILKIENCE ® | D | C | D | D | D | D |
| EXAMPLE IV | A | A | A | B | B | B |

TABLE G-3
HOT BLOW DRY - NORMAL HAIR

| Specimen | Overall | Static | Shine | Manage | Soft | Body |
|---|---|---|---|---|---|---|
| AGREE ® | C | C | C | C | C | D |
| CLAIROL ® II | C | C | D | C | D | C |
| SILKIENCE ® | B | B | B | B | B | B |
| EXAMPLE IV | A | A | A | A | A | A |

TABLE G-4
HOT BLOW DRY DAMAGED HAIR

| Specimen | Overall | Static | Shine | Manage | Soft | Body |
|---|---|---|---|---|---|---|
| AGREE ® | C | C | D | C | C | C |
| CLAIROL ® II | D | D | C | D | B | D |
| SILKIENCE ® | B | B | B | B | D | B |
| EXAMPLE IV | A | A | A | A | A | A |

TABLE G-5
COLD BLOW DRY - NORMAL HAIR

| Specimen | Overall | Static | Shine | Manage | Soft | Body |
|---|---|---|---|---|---|---|
| AGREE ® | B | B | B | A | B | B |
| CLAIROL ® II | C | D | C | C | C | C |
| SILKIENCE ® | D | C | C | D | D | D |
| EXAMPLE IV | A | A | A | A | A | A |

TABLE G-6
COLD BLOW DRY - DAMAGED HAIR

| Specimen | Overall | Static | Shine | Manage | Soft | Body |
|---|---|---|---|---|---|---|
| AGREE ® | B | B | A | B | B | B |
| CLAIROL ® II | D | D | C | C | C | D |
| SILKIENCE ® | C | C | C | C | D | C |
| EXAMPLE IV | A | A | A | A | A | A |

As shown in Tables G, the conditioner of the present invention is as good or better than every other specimen in every category tested.

From the foregoing it is readily apparent that the invention herein described and illustrated achieves all of the foregoing objectives in a remarkably unexpected manner. It is of course understood that such modification, adaptation and alteration as may readily occur to the artisan when confronted by this disclosure are intended within the spirit of the invention which is limited solely by the scope of the claims appended hereto.

What is claimed is:

1. A substantially homogeneous oil-free, fatty alcohol-free hair conditioner base comprising, in weight percent, from about 0.5 to about 3.0 percent Laureth-4; from about 1 to about 4 percent Choleth 24; from about 0.1 to about 0.8 percent hydroxyethylcellulose; from about 0.4 to about 0.8 percent polyquaternium 10; and q.s. distilled water.

2. A hair care product for conditioning hair comprising the base of claim 1 and one or more grooming agents to provide body, hold, sheen, and shine; a preservative; and a fragrance.

3. A hair care product according to claim 2 containing a viscosity modifier.

4. A hair care product according to claim 3 in which said viscosity modifier comprises from about 0.5 to about 0.8 percent synthetic gum.

5. A hair care product according to claim 2 in which said grooming agent is selected from the group consisting of film forming hair styling polymers and copolymers of vinyl pyrrolidone and vinyl ether.

6. A hair care product according to claim 2 in which said grooming agent is a quaternized hydrolysate of collagen.

7. A hair care product according to claim 5 containing a viscosity modifier.

8. A hair care product according to claim 7 in which said viscosity modifier comprises from about 0.5 to about 0.8 percent synthetic gum.

9. A hair care product according to claim 6 containing a viscosity modifier.

10. A hair care product according to claim 9 in which said viscosity modifier comprises from about 0.5 to about 0.8 percent synthetic gum.

11. A hair care product according to claim 2 containing an ingredient selected from the group consisting of sodium pyroglutamate, glycerin, soluble collagen, hydrolyzed animal protein, Quaternium 76 Hydrolyzed Animal protein, panthenol, quaternized hydrolysate of collagen and steapyrium chloride (Quaternium 7).

12. A hair care product according to claim 11 in which said ingredient is Quaternium 76 Hydrolyzed Animal protein.

13. A hair care product according to claim 11 in which said grooming agent is selected from the group consisting of film forming hair styling polymers and copolymers of vinyl pyrrolidone and vinyl ether.

14. A hair care product according to claim 12 in which said grooming agent is selected from the group consisting of film forming hair styling polymers and copolymers of vinyl pyrrolidone and vinyl ether.

15. A hair care product according to claim 11 in which said grooming agent is a quaternized hydrolysate of collagen.

16. A hair care product according to claim 12 in which said grooming agent is a quaternized hydrolysate of collagen.

17. A hair care product according to claim 11 containing a viscosity modifier.

18. A hair care product according to claim 17 in which said viscosity modifier comprises from about 0.5 to about 0.8 percent synthetic gum.

19. A hair care product according to claim 12 containing a viscosity modifier.

20. A hair care product according to claim 19 in which said viscosity modifier comprises from about 0.5 to about 0.8 percent synthetic gum.

21. A hair care product according to claim 13 containing a viscosity modifier.

22. A hair care product according to claim 14 containing a viscosity modifier.

23. A hair care product according to claim 21 in which said viscosity modifier comprises from about 0.5 to about 0.8 percent synthetic gum.

24. A hair care product according to claim 22 in which said viscosity modifier comprises from about 0.5 to about 0.8 percent synthetic gum.

25. A hair care product according to claim 2 further comprising a cationic conditioning agent selected from the group consisting of Polyquaternium-5, Polyquaternium-7, Steapyrium Chloride (Quaternium 7), Polyquaternium-11, Quaternium 26, Olealkonium Chloride and Cetrimonium Chloride.

26. A hair care product according to claim 3 further comprising a cationic conditioning agent selected from the group consisting of Polyquaternium-5, Polyquaternium-7, Steapyrium Chloride (Quaternium 7), Polyquaternium-11, Quaternium 26, Olealkonium Chloride and Cetrimonium Chloride.

27. A hair care product according to claim 5 further comprising a cationic conditioning agent selected from the group consisting of Polyquaternium-5, Polyquaternium-7, Steapyrium Chloride (Quaternium 7), Polyquaternium-11, Quaternium 26, Olealkonium Chloride and Cetrimonium Chloride.

28. A hair care product according to claim 6 further comprising a cationic conditioning agent selected from the group consisting of Polyquaternium-5, Polyquaternium-7, Steapyrium Chloride (Quaternium 7), Polyquaternium-11, Quaternium 26, Olealkonium Chloride and Cetrimonium Chloride.

29. A hair care product according to claim 11 further comprising a cationic conditioning agent selected from the group consisting of Polyquaternium-5, Polyquaternium-7, Steapyrium Chloride (Quaternium 7), Polyquaternium-11, Quaternium 26, Olealkonium Chloride and Cetrimonium Chloride.

30. A hair care product according to claim 12 further comprising a cationic conditioning agent selected from the group consisting of Polyquaternium-5, Polyquaternium-7, Steapyrium Chloride (Quaternium 7), Polyquaternium-11, Quaternium 26, Olealkonium Chloride and Cetrimonium Chloride.

31. A substantially homogeneous oil-free, fatty alcohol-free hair conditioner formulation comprising, in weight percent, from about 0.5 to about 3.0 percent Laureth-4; from about 1 to about 4 percent polyethylene glycol (24) cholesterol ether (Choleth 24); from about 0.1 to about 0.8 percent hydroxyethylcellulose; from about 0.1 to about 2 percent polyethylene glycol (16) lanolin ether; from about 0.4 to about 0.8 percent Polyquaternium 10; from about 1 to about 4 percent Quaternium 76 Hydrolyzed Animal protein; from about 0.2 to about 0.8 percent polyvinyl pyrrolidone; from about 0.1 to about 0.15 percent methylparaben; about 0.05 percent propylparaben; about 0.1 to about 0.3 percent imidazolidinyl urea; about 2 to about 8 percent propylene glycol; about 0.2 to about 0.3 percent fragrance and q.s. purified water.

* * * * *